United States Patent [19]

Dutton, Jr.

[11] 4,055,988
[45] Nov. 1, 1977

[54] ALIGNMENT CONTROL APPARATUS FOR A TURNTABLE USED IN AN ULTRASONIC TESTING SYSTEM

[75] Inventor: Arthur L. Dutton, Jr., Westport, Conn.

[73] Assignee: J. B. Engineering and Sales Company, Inc., Greenwich, Conn.

[21] Appl. No.: 748,960

[22] Filed: Dec. 9, 1976

[51] Int. Cl.² ............................................ G01N 29/04
[52] U.S. Cl. ........................................ 73/620; 73/629
[58] Field of Search .............. 73/67.5 R, 67.6, 67.8 S, 73/71.5 US

[56] References Cited

U.S. PATENT DOCUMENTS 3,614,890  10/1971  Bates ............................. 73/71.5 US

FOREIGN PATENT DOCUMENTS 1,595,825  7/1970  France ............................ 73/67.8 S Primary Examiner—Richard C. Queisser
Assistant Examiner—John P. Beauchamp
Attorney, Agent, or Firm—St. Onge, Mayers, Steward & Reens

[57] ABSTRACT

An alignment control is described whereby the orientation of a turntable can be adjusted from outside of a tank in which an ultrasonic test system operates. The alignment control employs a diaphragm which is mounted over an opening in the bottom of the tank and is formed of a material capable of being flexed while supporting liquid inside the tank. The diaphragm is firmly gripped by a pair of clamp plates respectively located inside and outside of the tank. The clamp plates effectively support the turntable through a drive shaft and bearing with a pivot control connected between the outer clamp plate and an external segment of the tank. External alignment of the turntable as well as external rotational drive are advantageously provided.

10 Claims, 5 Drawing Figures

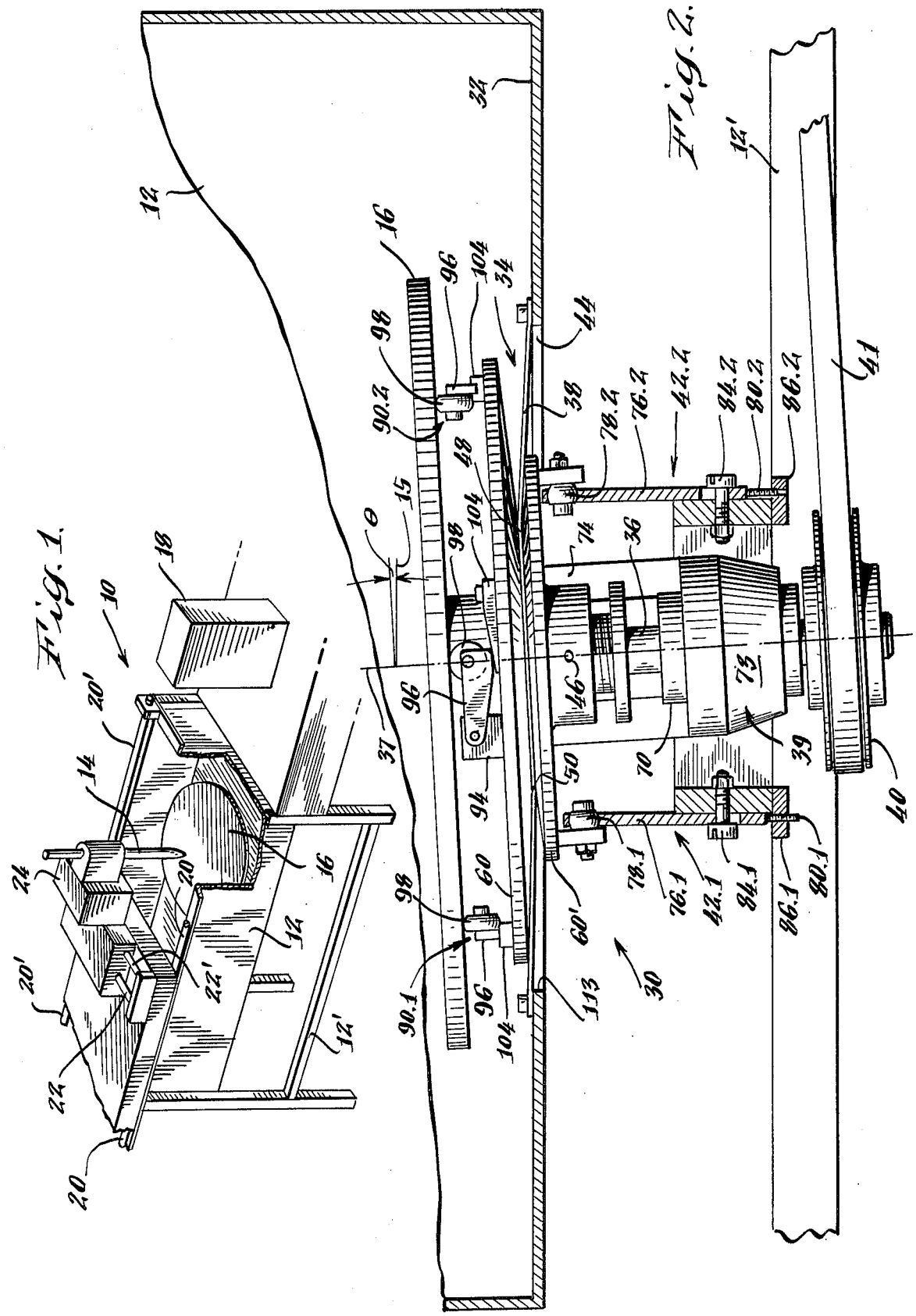

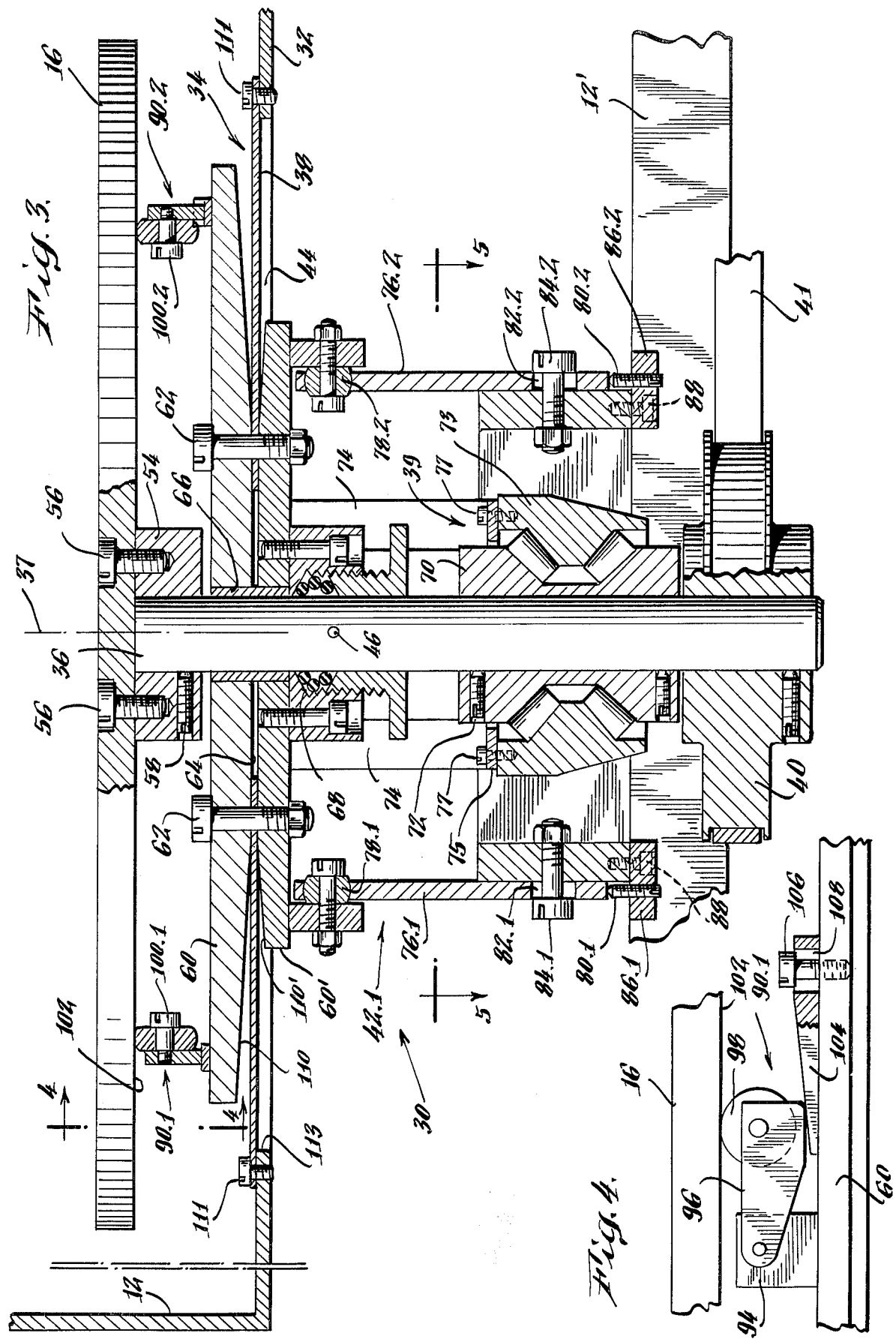

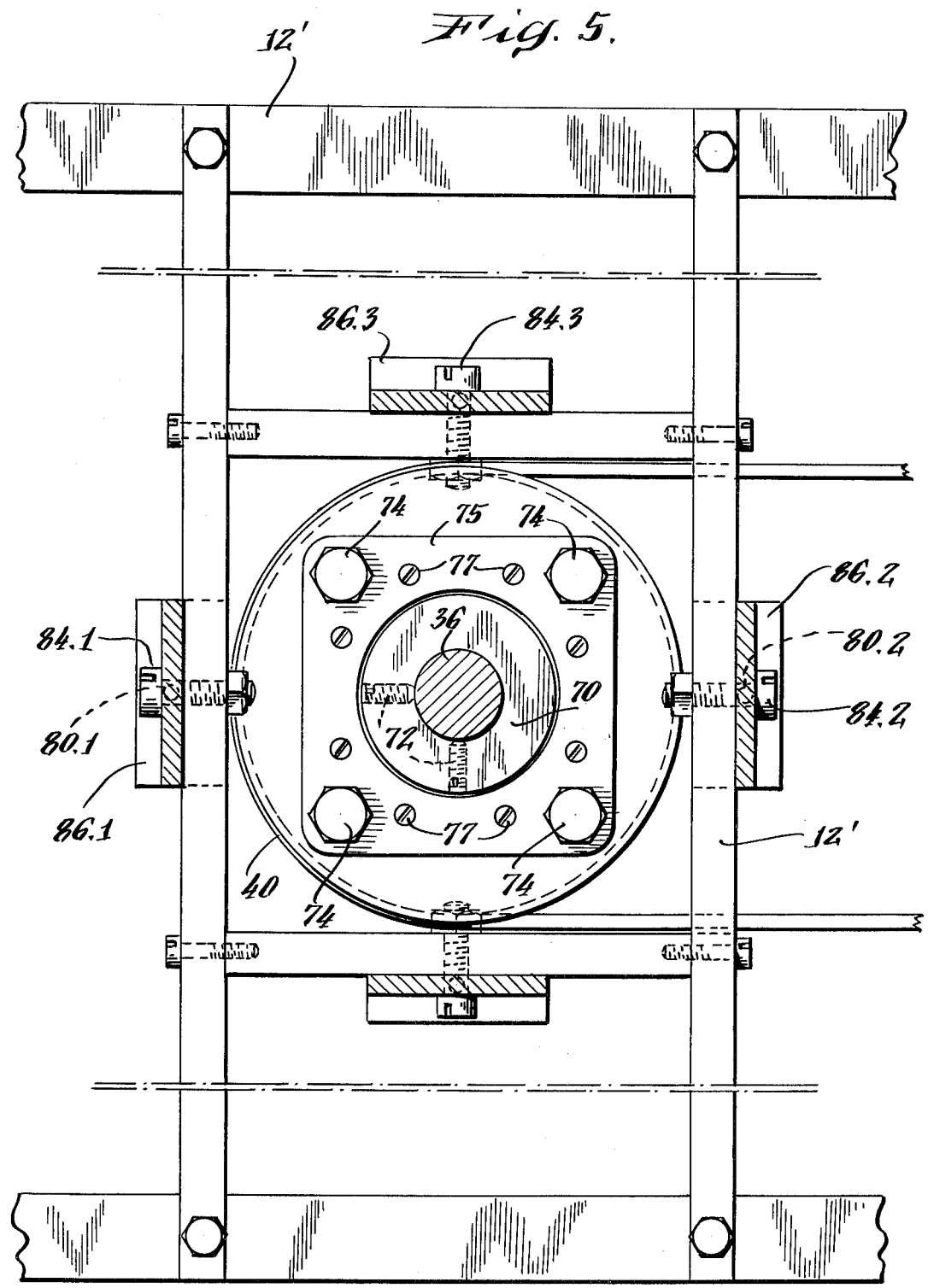

ALIGNMENT CONTROL APPARATUS FOR A TURNTABLE USED IN AN ULTRASONIC TESTING SYSTEM

This invention relates to a control for a platform used to orient a workpiece relative to an inspection device in an isolated area. More specifically this invention relates to an apparatus for adjusting a turntable submerged in a tank for use in an ultrasonic workpiece testing system.

BACKGROUND OF THE INVENTION

The use of ultrasonic test equipment to inspect workpieces is well known, see for example the U.S. Pat. No. 3,828,609 to Furon et al. Typically, a workpiece is mounted on a turntable inside a tank, which is filled with a liquid such as water. An ultrasonic probe is mounted so that it will direct ultrasonic energy onto the workpiece. The typical ultrasonic testing system, such as may be used to inspect aircraft engine parts, the turntable is rotated while submerged in a water filled tank and the ultrasonic probe moved, in a scanning plane, relative to the workpiece. The turntable drive components as well as supports and adjustments needed to orient the turntable are all located inside the tank.

Such prior art ultrasonic testing system has several undesirable features. For example, the turntable has to be elevated above the bottom of the tank (thus requiring a large and deep tank) to provide adequate room for controls and linkages needed to adjust the orientation of the turntable and provide rotational drive. Angular adjustments to the turntable are difficult to make in a deep tank and frequently require that the tank first be drained. As a result, accurate parallel alignment between the plane of rotation of the turntable with respect to the scanning plane of the ultrasonic probe is difficult to achieve. In addition, the water environment inside the tank is not compatible with the components used to control and drive the turntable so that bearings and similar components may quickly deteriorate, thus requiring more frequent replacement and maintenance.

SUMMARY OF THE INVENTION

With a platform control apparatus in accordance with the invention, a platform is located within an isolated area such as a tank while orientation controls and drives to rotate the platform are located external of the area. The platform can be adjusted for the correct orientation in a convenient manner without requiring access inside of the area where the platform is used to hold a workpiece.

As described with reference to one form for a control in accordance with the invention, a submergible turntable is mounted near the bottom of a tank for use in an ultrasonic testing system. The tank bottom has a substantial opening for access to and control of the turntable located inside the tank. The bottom opening is covered with a diaphragm formed of a sheet material capable of limited flexure outside of the mounting plane of the diaphragm. The diaphragm has sufficient strength to retain the liquid needed inside the tank for ultrasonic testing.

A support device is employed which firmly clamps the diaphragm along a continuous area about a generally central access opening therein. The support device is coupled to the turntable in a manner whereby the latter may be freely driven in rotation while its axis may be tilted to align the plane of rotation of the turntable by adjusting the orientation of the support device. The latter is, therefore, connected through a pivot control mechanism to the outside of the tank such as its external support frame.

The degree of tilt required for the turntable is determined by the amount of misalignment between the scanning plane of the ultrasonic probe and the plane of rotation of the turntable. Generally such misalignment is limited so that it can be compensated for by tilting of the support device relative to the mounting plane of the diaphragm. The latter, being firmly clamped to the support device, yields with a flexure to this tilt without disturbing liquid seals.

With the pivot controls outside the tank, a convenient external adjustment can be made to the orientation of the turntable which is located inside the tank. Furthermore, the rotational drive for the turntable may also be located outside the tank by employing a turntable drive shaft which extends through aligned access openings in the diaphragm support device and the tank bottom. A bearing is connected between the drive shaft and the support device so that the turntable may rotate within the tank while the support device remains stationary in its aligned position.

It is, therefore, an object of the invention to provide an accurate and convenient alignment control for a turntable used for ultrasonic testing of workpieces.

These and other advantages and objects of the invention may be understood from the following detailed description of a preferred embodiment described in conjunction with the drawings.

BRIEF DESCRIPTION OF DRAWINGS

FIG. 1 is a perspective view of a portion of an ultrasonic testing system which employs a turntable mounted with an alignment control apparatus in accordance with the invention on an ultrasonic testing tank;

FIG. 2 is a partially cut away side view in elevation of the turntable alignment control apparatus in extreme inclined position within the ultrasonic testing tank;

FIG. 3 is a central section view of the turntable mechanism in accordance with the invention;

FIG. 4 is a side view of a portion of the turntable taken along a plane defined by the line 4—4 in FIG. 3; and FIG. 5 is a section view of the turntable as taken along the plane defined by the line 5—5 in FIG. 3;

DETAILED DESCRIPTION OF EMBODIMENT

With reference to FIG. 1, an ultrasonic testing system 10 is shown including a large tank 12 for holding a suitable liquid such as water which serves to transmit ultrasonic energy from a probe 14 towards a workpiece (not shown) to be mounted on a rotational turntable 16. As the turntable 16 is rotated relative to the probe 14, ultrasonic energy from the latter is directed through the tank liquid towards the workpiece and echoes therefrom recorded with a recording device 18 mounted adjacent to the tank 12.

The ultrasonic probe 14 is mounted for movement in a scanning plane 15 as defined by mutually orthogonal slides 20, 22 located on the top of the tank. Equipment 24 to power the ultrasonic probe 14 is mounted to move on sides 22-22' so that the probe 14 can scan the entire area of turntable 16.

When a workpiece, which is mounted on turntable 16, is rotated by it in a plane of rotation relative to the scanning plane of the probe 14, care must be taken that the latter plane and the rotational plane of the turntable 16 are as parallel as possible. Small deviations from such parallelism disturb the recognition of workpiece defects. Since bulky and heavy workpieces are ultrasonically tested, the tank 12 and its associated external support frame 12' are formed of heavy gauge metal to reduce distortion.

With the alignment control apparatus 30 in accordance with the invention and as illustrated in FIG. 2, the turntable 16 may be conveniently and accurately aligned with the scanning plane of the probe 14. Furthermore, the turntable may be mounted close to the bottom wall 32 of tank 12 to thereby use its depth more efficiently. The control apparatus 30 enables an angular adjustment of turntable 16 while the mechanism for this and the rotational drive are mounted on the frame 12' external to the tank 12.

The alignment control apparatus 30 illustrated in FIG. 2 includes a support assembly 34 which vertically supports the turntable 16. A drive shaft 36 rotates about an axis 37 and extends from the turntable 16 through a diaphragm 38, the support assembly 34 and a bearing 39 to a pulley 40 for connection to a rotational drive (not shown) via a belt 41. A pivot mechanism 42 is interconnected between the support assembly 34 and the external frame 12' of the tank 12 to adjust the angular orientation of the turntable 16.

The bottom 32 of tank 12 is provided with a substantial aperture 44 which is covered by the diaphragm 38 mounted to the bottom wall 32 in liquid sealing relationship. The support assembly 34 firmly grips a central region of the diaphragm 38. The diaphragm 38 is made of a sufficiently thin material capable of limited flexure to enable an angular pivot of the turntable about a pivot point 46 as illustrated in FIG. 2. The location of the pivot 46 is preferably controlled to locate the pivot near the rotational axis 37. In this manner one segment of the diaphragm at 48 can be flexed upwardly while a diaphragm segment 50 is correspondingly flexed downwardly to achieve the desired tilt angle θ.

The magnitude of the tilt angle θ shown in FIG. 2 is somewhat slightly exaggerated for illustrative purposes. Also, the tilt angle θ is shown for a pivot movement about a pivot axis which is transverse to the plane of the drawing. A similar tilt may be accommodated about a pivot axis which lies in the plane of the drawing to provide the capability for correcting misalignments over a limited solid angle to achieve the desired parallelism between the scanning plane of the ultrasonic probe 14 and the plane of rotation of the turntable 16. Angular adjustments are made with four pivot controls 42, two of which are visible in view of FIG. 2.

As illustrated with greater detail with FIGS. 3, 4 and 5, the turntable 16 is attached to drive shaft 36 by a split hub 54 connected to turntable 16 with screws 56 and to the drive shaft 36 by set screws such as illustrated at 58. The drive shaft 16 extends through the support assembly 34 which is formed of a pair of circular clamping plates 60-60' respectively located on the inside and outside of tank 12. The clamp plates 60 are firmly connected to each other by bolts such as 62 to provide an annular gripping of diaphragm 38 about a central aperture 64 therein.

The engagement of clamp plates 60-60' provides a rigid support assembly with a liquid seal around aperture 64. The clamp plates 60—60' have a central aperture in alignment with aperture 64 so that drive shaft 36 can be passed through with a bushing 66 interposed between shaft 36 and the clamp plates 60 to allow the drive shaft to rotate relative to the clamp plates 60-60'. A packing gland 68 is employed around shaft 36 and below bushing 66 to provide a liquid seal.

The drive shaft further extends through bearing 39 which may be a double row tapered roller bearing having an inner ring 70 connected to the drive shaft 36 with suitable set screws 72. An outer ring 73 is connected by rigid bars 74 (see FIG. 5) to the outer clamp plate 60'. The bars 74 are connected to a rectangular plate 75, which in turn, is firmly bolted to outer ring 73 with screws 77. As a result, the entire turntable 16 is effectively supported by the inner and outer clamp plates 60-60' through bars 74, bearing 39 and drive shaft 36.

The outer clamp plate 60' in turn is connected to frame 12' of the tank 12 through pivot controls 42. Each pivot controls 42. Each pivot control 42 is formed of a vertically adjustable link 76 connected at one end through a spherical bearing 78 to the outer clamp plate 60'. The other end of each link 76 is controlled by an adjustment element by seating each link 76 on an adjustable set screw 80 mounted on frame 12'. Link 76 has a slot 82 through which a locking element such as a bolt 84 fits for firm connection to tank frame 12. When bolt 84 is loosened, vertical adjustment of the link 76 by set screws 80 can be made. The set screws 80 are aligned with links 76 by mounting each screw in a threaded bore of a flange 86 connected to the tank frame 12' with a bolt 88.

A misalignment between the plane of rotation and the scanning plane of ultrasonic probe 14 may be detected with conventional level techniques of variations in the output from probe 14 as it scans a rotating turntable without a workpiece. The sensed misalignment is corrected by loosening locking bolts 84 and adjusting set screws 80. It may be necessary to correct first for misalignment about one axis by adjusting set screws 80.1 and 80.2. Then, after testing for misalignment, a correction about the axis is made by adjusting set screws 80.3 and 80.4 (see FIG. 5). Adjustments may be conveniently done outside of tank 12. Preferably, each axis adjustment is carried out by moving one set screw up and the other down as illustrated in FIG. 2, thus maintaining the pivot 46 generally in the center. This procedure advantageously reduces the magnitude of the maximum flexure of diaphragm 38.

The inner and outer clamp plates 60-60' are formed of heavy gauge stainless steel so that their distortion when supporting a heavy workpiece is kept to a tolerable level. Since some workpieces are quite bulky and heavy, the turntable is preferably sufficiently large to support the workpieces. As a result, the turntable is also peripherally supported with vertically adjustable roller supports 90 along the periphery of mounted surface 92 of inner clamp plate 60.

As illustrated in FIG. 4, each roller support 90 is formed of a block 94 bolted to inner clamp plate 60 and provided with a roller control arm 96 which is pivotly mounted to block 94. A roller 98 is connected to arm 96 with a suitable screw 100 and brought into contact with the underside 102 of turntable 16 with a wedge 104. The wedge 104 in turn is mounted to inner clamp plate 60 with a screw 106 passing through a slot 108 in wedge 104.

The roller 98 preferably is provided with a contacting surface which supports in a yielding fashion. For example, a plastic covered roller can be used such that the turntable 16 can be peripherally supported without introducing a wobble and complex planar alignment procedures between all the roller supports 90.

Since the inner clamp plate 60 provides peripheral support to the turntable 16 with roller assemblies 90, the plate 60 is larger in area than outer clamp plate 60' and is provided with a cambered surface 110 facing and extending away from the diaphragm 38. Similarly, the outer clamp plate 60' has a cambered surface 110' also facing and extending away from diaphragm 38. The degree of camber is a function of the amount of pivot adjustment possible with the diaphragm 38. The inner clamp plate 60 may be so shaped and cambered to extend past the end 113 of tank opening 44. In such case the angle of camber can be selected to provide a positive safety stop against excessive tilting of the axis 37.

As illustrated in FIG. 2, the camber angle may be equal to the maximum tolerable pivot angle θ to provide a positive stop against excessive diaphragm flexure. The degree of flexure depends upon the type of diaphragm used and the maximum angular adjustment one may expect to require. An acceptable maximum angular adjustment capability (angle θ) needed may be about several degrees in which case the camber angle of surface 110 is at least as much to avoid interference.

A diaphragm formed of a sheet of stainless steel may be used. The thickness of the diaphragm sheet must be sufficiently thick to support the liquid in the tank, yet not too thick lest its ability to flex as shown in FIG. 2 is adversely affected. Generally a stainless steel sheet having a thickness in the range from about 0.015 inches to about 0.040 inches can serve as a practical diaphragm 38.

The degree of flexure is to some extent also influenced by the size of the opening 44 in tank bottom 32. A large opening permits a larger flexure than a smaller opening.

In one example for a turntable control apparatus 30, the bottom opening 44 was of the order of about 30 inches square and covered by a stainless steel diaphragm sheet of about 0.025 inches thick. The clamping engagement area as established by bolts 62 was distributed in a centrally located circle having a diameter of about 8 inches around diaphragm opening. The bottom opening 44 may be circular and the stainless steel diaphragm may be welded or bolted to bottom wall 32 with bolts such as 111. The connection between diaphragm 38 and bottom 32 is sealed against liquid leakage.

The diaphragm 38 can be made of a different material such as a flexible neoprene. In such case the neoprene must be made sufficiently thick to support the liquid inside tank 12 and resist accidental puncture.

When an angular alignment such as shown in FIG. 2 is made, the belt drive 41 may be correspondingly adjusted. Generally, when the angular correction is but a fraction of a degree, the belt drive can maintain its rotational drive of shaft 36.

Having thus described a turntable alignment control for use in an ultrasonic test system in accordance with the invention, the advantages of the invention can be appreciated. Angular adjustment of the turntable can be conveniently accomplished outside of the ultrasonic testing tank while drive components are no longer exposed to the liquid inside the tank.

What is claimed is:

1. An apparatus for adjusting the orientation of a rotational turntable relative to a wall of a tank inside of which the turntable is located to support and move a workpiece relative to an ultrasonic testing system movably mounted to the tank for movement in a scanning plane to ultrasonically probe the workpiece when a liquid is in the tank, comprising a diaphragm mounted in a plane to said tank wall over an adjustment opening thereof, said diaphragm having an access opening and being effectively mounted in liquid sealing relationship with the tank wall, said diaphragm further being formed of a material selected to permit limited flexure of the mounted diaphragm relative to its mounting plane;

support means mounted to the diaphragm to firmly clamp the diaphragm around its access opening, said support means having sufficient rigidity to support the platform and workpiece, said support means further being provided with a drive shaft opening in alignment with the access opening in the diaphragm;

a drive shaft mounted to the turntable and extending through the openings in the support means and the diaphragm in operative and effective liquid sealing relationship with the support means;

bearing means operatively coupled between the support means and the drive shaft to permit rotation of the latter about an axis of rotation while enabling the support means to support the turntable and workpiece; and pivot control means operatively connected between the support means and an external segment of said tank to adjust the orientation of the support means whereby said turntable orientation may be adjusted relative to the scanning plane of the ultrasonic testing system from outside of said tank.

2. The apparatus for adjusting the orientation of the rotatable turntable as claimed in claim 1 wherein the support means further includes an inner clamp plate and an outer clamp plate respectively mounted in liquid sealing relationship to opposite sides of the diaphragm, both of said plates being apertured and aligned with the access opening in the diaphragm to provide said drive shaft opening.

3. The apparatus for adjusting the orientation of the rotatable turntable as claimed in claim 2 wherein the clamp plates have cambered surfaces facing the diaphragm and extending away therefrom to enable pivot movement of the clamp plates.

4. The apparatus for adjusting the orientation of the turntable as claimed in claim 1 wherein the diaphragm is formed of a metal sheet having a thickness sufficient to support liquid in the tank and further being sufficiently thin to enable limited flexure in response to pivotal adjustment of the support means.

5. The apparatus for adjusting the orientation of the turntable as claimed in claim 4 wherein the diaphragm is formed of a stainless steel sheet material with a thickness generally in the range from about 0.015 inches to about 0.040 inches.

6. The apparatus for adjusting the orientation of the turntable as claimed in claim 5 wherein the support means further includes a plurality of adjustable roller assemblies adjustably mounted on the inner clamp plate for roller contact with a peripheral area of the turntable for its support against deformation when a workpiece is located on the turntable.

7. The apparatus for adjusting the orientation of the turntable as claimed in claim 6 wherein the roller assemblies are each formed of a block mounted on the inner clamp plate;

a pivot arm pivotly attached to the block for pivot movement between the clamp plate and the turntable;

a roller formed with a deformable rolling surface and rotatably mounted on the pivot arm; and a wedge mounted on the inner clamp plate for operative placement between the pivot arm and the clamp plate to bring the roller into supportive engagement with the turntable.

8. The apparatus for adjusting the orientation of the turntable as claimed in claim 1 wherein the pivot controls means includes a plurality of pivot controls uniformly distributed about the axis of rotation of the drive shaft to provide angular adjustments of the support means about a pair of mutually orthogonal axes.

9. The apparatus for adjusting the orientation of the turntable as claimed in claim 8 wherein each pivot control is formed of a control link resting on the external segment of the tank;

an adjustment element interposed between the link and the external frame; and a spherical bearing interposed between the link and the support means to enable relative pivot movement therebetween.

10. The apparatus for adjusting the orientation of the turntable as claimed in claim 9 wherein each control link is provided with an adjustment slot generally aligned with the external segment of the tank and a locking element extending through the slot and being sized to lock the adjusted link into firm engagement with the external tank segment.

* * * * *